United States Patent [19]

Siiman et al.

[11] Patent Number: 5,248,772
[45] Date of Patent: Sep. 28, 1993

[54] FORMATION OF COLLOIDAL METAL DISPERSIONS USING AMINODEXTRANS AS REDUCTANTS AND PROTECTIVE AGENTS

[75] Inventors: Olavi Siiman, Davie; Alexander Burshteyn, Miami Lakes, both of Fla.

[73] Assignee: Coulter Corporation, Miami, Fla.

[21] Appl. No.: 827,347

[22] Filed: Jan. 29, 1992

[51] Int. Cl.$^5$ .............. C08B 37/02; C07H 23/00; A61K 43/00; A61K 49/00

[52] U.S. Cl. .............. 536/112; 252/62.53; 252/62.54; 536/121; 424/1.1; 424/7.1; 424/9; 424/85.8; 424/94.1; 424/94.3; 424/94.67; 424/460; 424/461; 424/491; 424/493; 424/617; 424/618; 424/646; 424/649

[58] Field of Search ............... 536/112, 121; 252/62.53, 62.54; 424/9, 7.1, 1.1, 460, 461, 491, 493, 85.8, 94.1, 94.3, 94.67, 617, 618, 646, 649

[56] References Cited

U.S. PATENT DOCUMENTS

| | | | |
|---|---|---|---|
| 3,970,518 | 7/1976 | Giaever | 195/1.5 |
| 4,010,038 | 3/1977 | Iwasaki et al. | 427/338 |
| 4,267,234 | 5/1981 | Rembaum | 252/62.54 |
| 4,452,773 | 6/1984 | Molday | 424/1.1 |
| 4,578,350 | 3/1986 | Armenta et al. | 435/188 |
| 4,582,622 | 4/1986 | Ikeda et al. | 252/62.53 |
| 4,588,697 | 5/1986 | Khanna et al. | 436/518 |
| 4,680,338 | 7/1987 | Sundoro | 436/532 |
| 4,752,567 | 6/1988 | De Brabander et al. | 435/7 |
| 4,774,191 | 9/1988 | Khanna et al. | 436/528 |
| 4,795,698 | 1/1989 | Owen et al. | 435/4 |
| 4,806,488 | 2/1989 | Berger et al. | 436/536 |
| 4,891,324 | 1/1990 | Pease et al. | 436/519 |
| 4,920,061 | 4/1990 | Poynton et al. | 436/526 |
| 4,925,648 | 5/1990 | Hansen et al. | 424/9 |
| 4,935,147 | 6/1990 | Ullman et al. | 435/261 |
| 4,965,007 | 10/1990 | Yudelson | 252/62.53 |
| 5,057,313 | 10/1991 | Shih et al. | 424/9 |
| 5,062,991 | 11/1991 | Siiman et al. | 252/315.2 |

OTHER PUBLICATIONS

D. Hicks et al., "Localization of Lectin Receptors on Bovine Photoreceptor Cells Using Dextran-Gold Markers", *Invest. Opthalmol. & Vis. Sci.* 26: 1002-1013 (1985).

E. Matijevic, "Monodispersed Metal (Hydrous) Oxides-A Fascinating Field of Colloid Science", Acc. Chem. Res. 14: 22-29 (1981).

T. Sugimoto, "Preparation of Monodispersed Colloidal Particles", *Adv. Colloid & Interface Sci.* 28: 65-108 (1987).

T. W. Smith et al.; "Functional Polymers in the Generation of Colloidal Dispersions of Amorphous Selenium", *Macromolecules* 13: 1203-1207 (1980).

R. J. Mrsny et al., "A Novel Approach to the Ultrastructural Localization of Cell Surface Receptors: Affinity-Gold of Na, K-ATPase", *Eur. J. Cell Biol.* 45: 200-208 (1987).

J. J. M. Van Dongen et al., "Triple Immunological Staining with Colloidal Gold, Fluorescein and Rhodamine as Labels", *J. Immunol. Meth.* 80: 1-6 (1985).

R. Festin et al., "Detection of triple . . . using colloidal gold, fluorescein and fluorescein and phycoerythrin as labels", J. Immunol Meth. 101: 23-28 (1987).

*Primary Examiner*—Ronald W. Griffin
*Attorney, Agent, or Firm*—Silverman, Cass & Singer, Ltd.

[57] ABSTRACT

The invention related generally to the preparation of colloidal metal(O) particles having a crosslinked aminodextran coating with pendent amine groups attached thereto. The aminodextran acts as both a reductant for reducing metal ions to metal(O) particles and as the protective agent which coats the metal(O) particles thus formed. After stabilizing the aminodextran coating by use of a crosslinking agent, the coated particles can be used to covalently bind proteins. The resulting protein containing colloidal particles can be used as markers in optical and electron microscopy, in immunological and biological assays, and possibly as therapeutic agents.

37 Claims, 4 Drawing Sheets

FORMATION OF COLLOIDAL METAL DISPERSIONS USING AMINODEXTRANS AS REDUCTANTS AND PROTECTIVE AGENTS

RELATED INVENTION

This application is related to copending application Ser. No. 07/607,253 filed Oct. 31, 1990 entitled "BIODEGRADABLE PARTICLE COATINGS HAVING A PROTEIN COVALENTLY IMMOBILIZED BY MEANS OF A CROSSLINKING AGENT AND PROCESSES FOR MAKING SAME". These applications are owned by a common assignee.

FIELD OF THE INVENTION

This invention relates generally to a method for the preparation of stable colloidal metal particles having a crosslinked polysaccharide coating with functional groups attached thereto. More specifically, the invention is directed to a method for preparing selected colloidal metal particles, using an aminodextran as both the metal ion reductant and the protective coating agent for the colloidal particles produced, the aminodextran coated on the particles being stabilized by use of crosslinking agents.

BACKGROUND OF THE INVENTION

Metal ions in solution are attracted to the vicinity of functionalized polymer molecules. The reduction of the metal ions to metal(O) atoms creates a condition of super-saturation with respect to metal(O) atoms at a given polymer site. Consequently, the nucleation of metal particles proceeds in the local domain of the individual polymer molecules. Steric repulsion between different polymer-metal domains keeps the domains separated while attractive force between the polymer's functional groups and metal atoms on a particle keeps the particle in a single domain. The net effect is the immobilization of metallic nuclei by individual polymer molecules and the prevention of metal(O) particle growth by coagulation, i.e., nuclei from different polymer molecules are prevented from migrating and coagulating to form larger particles.

While polymer molecules may prevent metal(O) particle growth by coagulation, particle growth can occur by the diffusion of metal ions to the vicinity of the metal(O) particle nuclei. The growth of the particles is terminated when the solution is depleted of metal ions capable of migration. The metal(O) particles that are formed are uniform in size and shape. Further information on homogeneous precipitation, may be found in A. E. Nielsen, "Kinetics of Precipitation" (McMillan, New York 1964); E. Matijevic, Accts. Chem. Res., 14: 22 (1981); and T. Sugimoto, Adv. Coll. Interface Sci., 25: 65–108 (1987).

Colloidal dispersions of different metals have been prepared through a judicious choice of polymer, metal ion, reducing agent, the selective concentrations of the various ingredients and the temperature at which the reactions are carried out. Simple alcohols such as methanol or ethanol have been used as both solvent and reductant in the presence of a protecting polymer such as PVA (polyvinyl acetate). Polyols, ethylene glycol and diethylene glycol have been used similarly as both solvent and reductant. Functionalized polymers such as hydrazinium polyacrylate have been used as both reductant and protecting polymer in the preparation of monodispersed particles of gold, silver, copper, platinum and selenium. Tannin, which contains one to three trihydroxybenzenecarboxylate groups on a sugar, usually glucose, can act as both a reducing agent and a protecting substance during the formation of gold hydrosols. For examples, see L. Hernandez et al, J. Colloid Sci., 3: 363–375 (1948) (rhodium-polyvinyl acetate [Rh-PVA] polymer using hydrogen as reductant); H. Thiele et al, J. Colloid Sci., 20: 679–695 (1965) (hydrizide of polyacrylic acid (PAH)-Au, Ag, Cu, Pt and polyethyleneimi acid-Au); H. Harai et al, J. Macromol. Sci. Chem., A12: 1117–1141 (1978) (Rh-PVA using methanol as reductant); H. Harai et al., J. Macromol. Sci. Chem., A13: 633–649 (1979) (Rh-, Pd-, Os-, Ir- and Pt- PVA using methanol as reductant); H. Harai et al, ibid., A13: 727–750 (1979) Rh-, Pd-, Ag-, Os-, and Ir-PVP using ethanol as reductant); F. Fievet et al, MRS Bulletin, December, 1989, pp. 29–34 (Au-, Ag-, Pd-, Pt-, Cu-, Co-, Ni-, Cd- and Pb-Polyol); O. Siiman et al., J. Chem. Soc. Faraday Trans., 82: 851–867 (1986) (Au-PVP-ethanol); H. B. Wieser, "Inorganic Colloid Chemistry, Vol. I, The Colloid Elements" (Wiley, New York (1933)) (tannin-Au); T. W. Smith et al., Macromol., 13: 1203–1207 (1980) (Se-PA hydrazine) and T. W. Smith et al., J. Phys. Chem., 84: 1621–1629 (1980) (Fe-polymer).

Colloidal gold has been used frequently as an adsorbent for antibodies, enzymes, lectins and other proteins, primarily because of the non-specific nature of protein adsorption on colloidal gold. Virtually any protein material may be adsorbed onto colloidal gold. Protein-gold species, maintained in an active state, have found use as cell surface markers in optical and electron microscopy. [See "Colloid Gold: Principles, Methods and Applications", Vols. I, II and III, M. A. Hayat, ed. (Academic Press, New York 1989) and A. J. Verkleij and J. L. M. Leunissen, "Immuno-Gold Labelling In Cell Biology" (CRC Press, Boca Raton, Fla. 1989)]. The detection of colloidal metal particles of 10–100 nm diameter in light microscopy by epi-illumination with polarized light is described in U.S. Pat. No. 4,752,567 to M. J. De Brabander et al. Of particular interest are colloidal gold particles having directly or indirectly adsorbed antibodies. Indirect adsorption is accomplished by binding the antibody to a first adsorbed layer; for example, a secondary antibody, avidin, or protein A or G. Ligand-dextran complexes have been adsorbed onto colloidal gold. The ligands included lectins, concanavalin A, Ricinus communis agglutinin and wheat germ agglutinin [D. Hicks and R. S. Molday, Invest. Opthalmol. Vis. Sci., 26: 1002–1013 (1985)] and ouabain [R. J. Mrsny et al., Eur. J. Cell Biol., 45: 200–208 (1987)].

However, the adsorption of proteins onto colloidal gold particles in aqueous solution is a reversible equilibrium reaction. Particle adsorbed protein and unabsorbed or free protein are separated, usually by centrifugation. However, after separation and removal of the free protein, and resuspension of the purified protein-gold colloid, further loss of adsorbed material occurs as equilibrium re-establishes itself. Consequently, long term storage of purified adsorbed protein-gold conjugates has not been practical. Some workers in the field have suspended the purified protein-gold colloids in buffer solutions containing blocking agents such as bovine serum albumin (BSA), polyvinyl pyrrolidone (PVP), polyethylene glycol (PEG) and other polymeric materials in an attempt to increase stability. The polymeric materials serve to cover any remaining exposed areas on the surface of the colloidal gold particles and thus prevent aggregation of gold particles. However, the polymeric material is present in large excess over the adsorbed protein on the colloidal gold and competes with the protein for colloidal gold sites. Inevitably, some desorption of protein from gold will occur and free protein will be present again in the solution.

It is an object of the invention to prepare colloidal metal particles, preferably colloidal gold or silver particles, having a stabilized coating of a polysaccharide material. Another object of the invention is to use such coated colloids to prepare stable protein-colloid conjugates. The protein-colloid conjugates of the invention overcome the instability and orientation problems associated with proteins which are adsorbed directly on colloid metal surfaces.

SUMMARY OF THE INVENTION

The invention provides for the preparation of monodispersed colloidal metal(O) particles having a solid core and coated with an amine-derivatized polysaccharide, the coating being crosslinked or fixed by the action of a chemical crosslinking agent and having a plurality of pendent functional groups. The pendent functional groups may be aldehyde or carboxylate groups, amine groups, sulfhydryl or maleimidyl groups and polyclonal or monoclonal antibodies.

The invention provides a one step process for preparing coated colloidal metal(O) particles by heating an aqueous solution of a metal salt with an amino-derivatized polysaccharide having at least one reducible sugar component and preferably a plurality of reducible sugar components, for a time and at a temperature sufficient to reduce the metal salt to a metal(O) particle and simultaneously coat the particle with the polysaccharide. Subsequently, the coated particle is treated with a bifunctional crosslinking agent, preferably gluteraldehyde, a diamine, preferably 1,3-diaminopropane, and a reducing agent, preferably sodium borohydride, and purified to give a stabilized, amine derivatized polysaccharide coated metal(O) particle. The polysaccharide acts as both a reducing agent for the metal ions and as the coating agent for the zero-valent colloidal metal particles that are formed. The resulting coated and stabilized colloidal metal particles may then be conjugated with proteins such as enzymes, lectins, polyclonal or monoclonal antibodies and the like. These proteins may or may not have attached thereto detectable labels such as dyes, compounds containing radioactive elements, electron dense elements, enzymes and the like. The resulting protein-containing colloidal metal(O) conjugates may be used in a variety of diagnostic and assay procedures.

DETAILED DESCRIPTION OF THE INVENTION

Described herein is the preparation of polysaccharide coated colloidal metal(O) particles that have particular advantages for the conjugation of antibodies and other proteins. Aminodextran is the preferred polysaccharide. Dextran, as used herein, refers to any branched polysaccharide of D-glucose, regardless of the branch point of the repeating unit; i.e., 1→2, 1→3, 1→4, etc. Aminodextran means any dextran that has been modified to have one or more amine ($NH_2$) groups. 1,3-Diaminopropane is the preferred diamine for avoiding intra- and inter-sugar residue crosslinking which would the negate amine functionalization of dextran.

A number of different, usually bifunctional, crosslinking agents such as bis[2-(succinimidooxycarbonyloxy)ethyl]sulfone, disuccinimidyl tartarate, ethylene glycol bis(succinimidylsuccinate), disuccinimidyl suberate and glutaraldehyde, can be used in practicing the invention. Common commercially available glutaraldehyde, the preferred crosslinking agent, usually contains mainly monomer absorbing at 280 nanometers (nm). However, this glutaraldehyde product also contains some polymeric species which gives rise to an absorbance at 235 nm. The polymeric species, probably trimers or linear oligomers, are of sufficient length to form intra- and inter-molecular bridges between amino groups present on the adsorbed aminodextran. By judicious selection of reaction conditions, the aminodextran can be suitably fixed on the colloidal core particles so the it will not be removed during subsequent manipulations. Large flocs created by excessive crosslinking of free aminodextran can thereby be avoided and interparticle crosslinking is negated.

In order to be useful in the biological and medical arts, the fixed or crosslinked aminodextran coating on the colloidal gold particles should contain functional groups which can be conjugated with biologically active substances. Covalent coupling of biological substances such as monoclonal antibodies to the coating is preferred over simple adsorption. The coupling of an antibody, either polyclonal or monoclonal, to the crosslinked aminodextran surface coating is accomplished by the use of "short chain" diamines or polyamines and a hetero-bifunctional reagent. (Hereafter the word diamine includes polyamines having three or more amine groups). The diamine is reacted with residual aldehyde or carboxylate groups, either naturally occurring or present by the steps of this invention, present on the surface of the crosslinked aminodextran surface. The diamine serves not only to block aldehyde and carboxylate groups, but also serves to replenish the amine groups that were reacted during the crosslinking process. The diamine reacts with aldehyde groups to form Schiff bases. The Schiff bases are then reduced to stable amine groups by reduction, preferably with sodium borohydride.

Short chain diamines are preferred in order to avoid crosslinking neighboring aldehyde or carboxylic acid groups on the same particle or to avoid linking such groups on different particles. One diamine group reacts with the coating surface and the other remains unreacted and available for coupling, directly or indirectly, to a protein material. In general, the diamine is selected from the group consisting of $H_2NCH_2-(CH_2)_x-CH_y(CH_3)_z-NH_2$ and $C_6H_{4+a}(NH_2)_2$, where $x=0-3$, $y=1$ or 2, and $z=1$ when $y=1$ or $Z=0$ when $y=2$; and a=0 or 6. Examples include ethylenediamine, phenylenediamine, propylenediamine, 1,4-cyclohexanediamine, cyclohexenediamine tetramethylenediamine and the like. Triamine amines include diethylene triamine 1,5-diamino-3-(2-aminoethyl)pentane and the like. Ethylenediamine is preferred.

The coupling of biological substances to the fixed, aminodextran coated colloidal gold particles involves activation of free amino groups with a water soluble heterobifunctional reagent such as 2-iminothiolane hydrochloride (IT), sulfosuccinimidyl-4-(N-maleimidomethyl)cyclohexane-1-carboxylate (sulfo-SMCC), m-maleimidosuccinimide ester, N-succinimidyl-3-(2-pyridyldithio)propionate, succinimidyl-4-(p-maleimidophenyl)butyrate, N-succinimidyl-(4-iodoacetyl)aminobenzoate, the reagents listed above as substitutes for glutaraldehyde and the like. The 2-iminothiolane hydrochloride and the maleimidyl and succinimidyl reagents are preferred. E. Ishikawa, Immunoassay Supp., 1:1–16 (1980) and J. Immunoassay, 4:209–227 (1983); M. Imagawa et al., J. Appl. Biochem., 4: 41–57 (1982) and M. D. Partis, J. Protein Chem., 2: 263–227 (1983). When using sulfo-SMCC, the active sulfosuccinimidyl ester end of sulfo-SMCC will react at pH 7.0–7.5 with amines to give peptide bonds. The sulfo-SMCC/diamine bridging unit which results is approximately 16 Angstroms in length.

The maleimidyl group of sulfo-SMCC will react at pH 6.5–7.5 with free sulfhydryl groups to form a stable, covalent thioether bond. However, it is essential that the coated particles which are reacted with sulfo-SMCC contain no free sulfhydryl groups which would react with the maleimidyl end of sulfo-SMCC. The use of aminodextran as a coating agent precludes such a problem because, unlike other coating materials such as gelatin, it does not have any free sulfhydryl groups.

Proteins, particularly either monoclonal or polyclonal antibodies, can be linked to the maleimidyl end of sulfo-SMCC functionalized, aminodextran coated gold colloids by means of sulfhydryl groups that are present on proteins either naturally or by derivatization. Proteins which have cysteinyl residues inherently contain sulfhydryl groups. To introduce additional sulfhydryl groups, the proteins' amine groups are activated with Traut's reagent, 2-iminothiolane hydrochloride (IT), at a pH in the range of 7–10. When the proteins are antibodies, antibody lysyl and terminal amine groups are activated by IT. M. Erecinska, Biochem. Biophys. Res. Commun., 76: 495–500 (1977); J. M. Lambert et al., Biochemistry, 17: 5406–5416 (1978); and M. E. Birnbaumer et al., Biochem. J. 181: 201–213 (1979).

When using the aminodextran coated gold colloids of the invention, it is useful to vary the reaction conditions and the concentration of reagents in order determine optimal coupling so that the protein, particularly when an antibody, will retain its maximum functional activity. Although maleimides react quite rapidly with sulfhydryl groups in solution, the same groups immobilized on particles should be allowed a given longer reaction time in order to assure completeness of reaction. Particle and antibody concentrations during antibody conjugation should be optimized to avoid aggregation, particularly when IgM antibodies are used. The optimized procedures for IgM antibodies can be used for all monoclonal antibodies with an isoelectric point range of about 5.0 to about 9.0. Generally, about 30-fold less antibody is required to achieve covalent coupling than is required for simple adsorption; a consequence of importance where expensive or hard to obtain antibodies are involved.

The invention eliminates separately preparing colloidal metal particles and subsequently preparing the colloids for polymer (coating) adsorption and crosslinking. These steps are combined in the method described herein by reacting metal salts with an oxidizable sugar containing amine derivatized polysaccharide such as an aminodextran for a time and at a temperature sufficient to reduce the metal salt to colloidal metal(O) particles and simultaneously coating the particles with the polysaccharide. The preferred temperatures are in the range of about 90°–100° C. In general, metal ions having a reduction potential of +0.7 volts ($H_3IO_6/IO_3^-$), or higher may be used according to the invention. [For examples see Handbook of Physics and Chemistry, 64th Ed. (CRC Press, Boca Raton, Fla. (1983–84), page D-156]. Gold and silver salts are preferred. Salts of Rh(III), Pd(II), Pt(II) and Ir(III) may also be used. Using gold and silver salts as non-limiting examples, an aminodextran compound used according to the invention assumes the following multiple roles in the formation of the colloidal metal particles and their subsequent reactions:

1. It is the reducing agent for converting Au(III) to Au(O) or Ag(I) to Ag(O) by oxidation of glucopyranose rings first to an aldehyde, —(OH)CH—CH(OH)—→2—CH(O)+2H$^+$, and subsequently to organic acid, 2CH(O)+2H$_2$O→2—COOH+2H$^+$.
2. It is the colloid protecting species due to the ability of the amino groups to interact strongly with metal ions or atoms. Furthermore, the amino groups coordinate with the cationic metal ions in solution, assume a positive charge and stabilize the cationic dispersion. Although dextran is capable of reducing Au(III) or Ag(I) ions, it will not stabilize the resulting colloid.
3. Crosslinkages can be formed during colloid formation between the aldehyde groups formed by oxidation of the sugar groups and amino groups already present on aminodextran to form Schiff bases, —HC=N—, which can further strengthen the particle-polymer complex.
4. Crosslinking agents such as glutaraldehyde can be used to further bridge metal(O) particle coating amino groups and encapsulate the colloidal particles so that they cannot be released by purely physical means. Proteins which are subsequently covalently bound to the crosslinked coating will not be separated from the colloidal metal particles by the equilibrium reaction described above.
5. Unreacted polymer amino groups and amino groups created by blocking unreacted aldehyde groups with a diamine serve as sites for binding antibodies and other proteins to the colloidal particle coating. Bridging groups may be used to between the protein and the coating amino groups.

The method of the invention is useful is preparing colloidal metal(O) particles in the size range of 5–100 nm diameter. The exact size of the particles formed will vary according to the concentration of the starting reagents used in the reaction (aminodextran, metal ion), the temperature of colloid formation, the rate of stirring the mixture of metal ion and aminodextran, and the average molecular weight of the aminodextran used in the reaction.

In practicing the invention, it should be considered that metallic particles pose particular problems with regard to covalent coupling methods. In particular, surface metal atoms or ions may be vulnerable to chemical reaction and leaching by the coupling, activating and blocking agents that are often used in the covalent binding of proteins to organic coatings. Some typical reagents used to bind proteins to organic coatings which may have this effect are iminothiolane, glutaraldehyde, ethylenediamine, cysteine, iodoacetamide and sulfosuccinimidyl-4-(N-maleimidomethyl)cyclohexane-1-carboxylate (sulfo-SMCC). Careful selection of reagents and control of their concentration must be exercised in practicing the invention. Even though a first layer of polymeric coating can often be easily applied to a metal particle, this does not eliminate the need to exercise precaution in subsequent use of the coated particles. Since small molecules can easily pass through the pores in a polymer layer, the surface of the metal particle is still accessible to these molecules.

The polymeric coating realized from employing the invention may not necessarily cover the entire surface of the colloidal metal particle. Consequently, particle aggregation remains a possibility. However, the occurrence of bare spots on the colloidal particles can be minimized by judicious choice of polymer concentration and molecular weight before fixation with a crosslinking agent. Aggregates are eliminated after several ultracentrafugings and redispersions of the coated gold colloid by rejection of any non-mobile residue. The size of the polymer should be smaller than the diameter of the colloidal metal particles. For 20 nm diameter gold particles, this means an average polymer molecular weight of about 40,000 daltons in order to prevent the polymer from causing bridging flocculation. The polymer molecules must surround the gold particles instead of the gold particles staining the polymer molecule. For gold particles of 20 nm diameter at a concentration of $10^{12}$ particles/mL, the polymer concentration should be in the range of about 0.1-2.5 mg/mL.

The optimum conditions for the reaction of activated gold particles with activated proteins such as monoclonal antibodies can be estimated from similar reactions with other colloidal particles. For example, to avoid aggregation of particles and obtain a good surface loading of monoclonal antibody on magnetic beads of 1 $\mu$m mean diameter, the particle concentration was $1.83-3.73 \times 10^8$ particles/cm$^3$ and the total antibody concentration was 0.313-0.625 mg/mL. This particle concentration gives a mean interparticle distance of 64-81 $\mu$m or 64-81 particle diameters. Colloidal gold particles of 20 nm diameter are typically prepared at a concentration of $1.30 \times 10^{12}$ particles/cm$^3$, yielding a mean interparticle distance of 0.92 $\mu$m or 46 particle diameters Consequently, a 3-6 fold dilution of the gold sol is necessary to operate under kinetic conditions similar to those of the magnetic particles.

DESCRIPTION OF THE PREFERRED EMBODIMENT

Example 1. Preparation of Aminodextran

Method 1. Small Scale Preparation of Aminodextran

Aminodextran was prepared by partial cleavage and oxidation of the glucopyranose rings in dextran to aldehyde functional groups, coupling of the aldehyde groups with 1,3-diaminopropane to form Schiff base linkages and reduction of the Schiff's base linkages to stable amino groups. In a typical procedure, 20 g of dextran were dissolved in 150 mL of 50 mM potassium acetate buffer, pH 6.5. A solution of 2.14 g of sodium periodate in 25 mL of distilled water was added dropwise to the dextran over about 10 minutes with vigorous magnetic mixing. The resulting solution was stirred at room temperature, 15°-27° C., for about 1.5 hours and then dialyzed against distilled water. 20 mL of 1,3-diaminopropane was mixed with 20 mL of distilled water, cooled in an ice bath, vigorously stirred and pH adjusted from about 11.5 to about 8.7 over about 15 minutes by the addition of glacial acetic acid. Typically, 15-20 mL of glacial acetic acid is used. The dialyzed dextran was added dropwise over about 15-20 minutes to the chilled diamine solution. After the addition was completed, the resulting solution was stirred at room temperature for about 2.25 hours. A reducing solution of 0.8 g sodium borohydride in 10 mL of 0.1 mM sodium hydroxide was added to the dextran reaction mixture at room temperature over about 15 minutes. The reaction mixture was stirred during the borohydride addition to expel most of the effervescence. The crude aminodextran solution was exhaustively dialyzed against distilled water until the conductivity of the effluent was 3-4 $\mu$mho/cm. The dialyzed solution was then filtered through an 0.2 $\mu$m filter and freeze-dried over 24 hours in a model TDS-00030-A, Dura-Dry microprocessor controlled freeze dryer (FTS Systems, Inc.) to produce 4.25 g of flaky, pale yellow crystals in 21% yield.

Method 2. Large Scale Preparation of Aminodextran

The procedure of Method 1 is modified for the large scale preparation of aminodextran and for increasing the number of amino groups introduced into dextran. Hollow fiber membrane filtration replaces dialysis and a smaller diamine-periodate molar ratio is used to avoid further cleavage of the sugar polymer into lower molecular weight fragments. A hollow fiber cartridge (polysulfone, 3 ft$^3$ membrane surface area, 1 mm diameter fibers and 5,000 MW cut-off) was mounted vertically with an input power pump (two pump heads, maximum flow rate of about 4.56 liters/minute with No. 18 Norprene food grade tubing) delivering 15-20 psi which corresponds to 5-10 psi in the retenate line. The filtrate is collected at 50-100 mL/min. Washing was done using 20-30 liters of distilled water over about 6-8 hours. The specific conductance was reduced to about 3-4 $\mu$mho-cm$^{-1}$ and the pH was 6.0-6.5. The feed volume was maintained at 2 liters during desalting and then concentrated to 800 mL in the first washing of oxidized dextran and to 400 mL in the second washing of aminodextran.

In a standard scaled-up preparation, 80 g of dextran were transferred to 1 quart [liter] glass blender bowl containing 600 mL of distilled water. The solid was blended for about 2-5 minutes at medium speed to dissolve all the dextran. 8.56 g of sodium periodate were dissolved in 100 mL of distilled water and the resulting solution was added dropwise to the dextran solution over about 10 minutes using vigorous magnetic stirring. After the addition was completed, the resulting mixture was stirred at room temperature for an additional 3 hours. The resulting viscous reaction mixture was then diluted to 2 liters with distilled water and desalted using a hollow fiber cartridge. The initial specific conductance was 1.5 mmho-cm$^{-1}$ or higher and the initial pH was 4.0. About 18-22 liters of distilled water was used to obtain a final specific conductance of about 3-4 $\mu$mho-cm$^{-1}$ and a final pH of 6.0-6.5. The final volume of washed, oxidized dextran solution was 800 mL.

To the washed, oxidized dextran solution, 80 mL of colorless, liquid 1,3-diaminopropane was slowly added over about 10 minutes at room temperature. The resulting mixture was then stirred at room temperature for an additional 3 hours. After the stirring was finished, 3.2 g of sodium borohydride dissolved in 40 mL of 1 mM aqueous sodium hydroxide was added to the room temperature aminodextran reaction mixture over about 5 minutes with magnetic stirring. After the completion of the sodium borohydride addition, the resulting mixture was stirred for an additional 1 hour and then desalted using a hollow fiber cartridge. The initial specific conductance was 5.0 mmho-cm$^{-1}$ or higher and the initial pH was about 12.0. About 20-25 liters of distilled water were needed to reduce the specific conductance to about 3-4 $\mu$mho-cm$^{-1}$ and the pH to 6.0-6.5. The final volume of aminodextran was 400 mL. This solution was passed through a 0.2 $\mu$m sterile cellulose acetate filter unit and then freeze-dried over 48 hours to obtain 48 grams of flaky, pale yellow crystals, a 52% yield.

Elemental analyses (C,H,N) were obtained for two samples of aminodextran prepared from dextran T-2M by the methods described above. The analyses are:

Sample 1. 20 g dextran scale, desalting by dialysis. Obsd.: C, 43.04; H, 6.60, N, 1.09; O (by difference), 49.27.

Sample 2. 80 g dextran scale, desalting by membrane filtration. Obsd.: C, 42.53; H, 6.52; N, 1.01; O (by difference), 49.94

Calculated for $C_{46}H_{79}NO_{37}\cdot 3H_2O$: C, 42 76; H, 6.63; N, 1.08; O, 49.53

The analyses for aminodextran in the two preparations were very similar, thus indicating that the same product was obtained whether desalting was done by dialysis or by membrane filtration. The empirical formula obtained for Sample 1, $C_{46}H_{84}NO_{40}$, is very similar to the formula $C_{46}H_{79}NO_{37}\cdot 3H_2O$ based on 29 units of glucose ($C_6H_{10}O_5$), 1 unit of fully diamine-substituted sugar ring ($C_{12}H_{28}N_4O_3$) and twelve units of water. Therefore, the degree of diamine substitution in dextran was 1/30 in Sample 1 in contrast to a theoretical value of 1/12 based on 100% periodate cleavage and diamine substitution. The empirical formula obtained for Sample 2, $C_{49}H_{90}NO_{43}$, is very to the formula $C_{49}H_{84}NO_{40}\cdot 3H_2O$ based on 31 units of glucose, 1 unit of fully diamine substituted sugar ring and twelve units of water. The degree of substitution in dextran by diamine was 1/32 for Sample 2.

Example 2. Preparation of Gold Hydrosol Using Aminodextran

A stock gold solution was prepared by dissolving 112.4 mg of HAuCl$_4$ (49% Au) in 1 L distilled water to give a 2.8$\times$10$^{-4}$M Au(III) solution. Stock Au(III) solution (380 mL) was brought to a boil, rapidly stirred and 45.0 mL of aminodextran concentrate (10.3 mg/mL) was added by pipette. The initial light purple of the mixture became wine red after about 1 minute. The mixture was boiled and stirred for a minimum of 15-20 minutes to complete the reaction and bring the total volume of the gold sol to 200 mL and the concentration of aminodextran to 2.3 mg/mL (0.23% w/v). Similar results were obtained using aminodextrans having average molecular weights of 10,000, 40,000 and 2,000,000 (T-10, T-40 and T-2M) with 1$\times$ (1$\times$=3.3% substitution of sugar residues), 2$\times$ (6.6%) and 3$\times$ (9.9%) molar amounts of amino groups. The 2$\times$ and 3$\times$ aminodextrans were obtained using 2 and 3 times the amount of sodium periodate used in the 1$\times$ oxidation of dextran described in Example 1. The amount of 1,3-diaminopropane used for Schiff base formation was kept constant.

The stoichiometry of the reactions is given by the following redox equations. The first equation involves the cleavage and oxidation of glucopyranose rings to an aldehyde and the reduction of Au(III) to Au(O).

$$2AuCl_4^- + 3\text{---(OH)CH---CH(OH)---} \rightarrow$$
$$2Au(O) + 8Cl^- + 6\text{---CH(O)} + 6H^+,$$

The second equation is for the oxidation of the aldehyde to carboxylic acid and reduction of Au(III) to Au(O).

$$2AuCl_4^- + 3CH(O) + 3H_2O \rightarrow 2Au(O) + 8Cl^-$$
$$+ 3\text{---COOH} + 6H^+.$$

The progress of converting Au(III) to Au(O) was followed by monitoring the absorption spectrum of the gold colloid in the visible region. Small gold particles of about 20 nm diameter typically show a maximum absorption at 520 nm in aqueous solution. A shift of this peak to longer wavelengths is indicative of larger particles or clustering of primary particles to form doublets, triplets, etc. Optimal aminodextran-gold molar ratios for producing single, polymer-stabilized particles were determined by analyzing the visible spectra of a series of preparations. FIGS. 1A-1D were obtained using 1$\times$ aminodextran, T-10 derived, concentrations of 0.005, 0.010, 0.015 and 0.020% w/v. Unreacted sugar units were, in mol, 1.49$\times$10$^{-5}$, 2.98$\times$10$^{-5}$, 4.47$\times$10$^{-5}$ and 5.95$\times$10$^{-5}$, respectively. 50 mL of stock Au(III) sol or 1.40$\times$10$^{-5}$ Au were used. The molar ratio of unreacted sugar to Au were about 1:1 (FIG. 1A), 2:1 (FIG. 1B), 3:1 (FIG. 1C) and 4:1 (FIG. 1D) respectively. The results shown in FIG. 1 indicate that a molar ratio of 3:1 or greater is required to obtain a stable aminodextran protected gold hydrosol. Using a lesser ratio results in the formation of aggregated particles.

Example 3. Reaction of Dextran with Chloroauric Acid 2.5 g of dextran T-40 was dissolved in 50 mL distilled water. 10 mL (3mmol sugar residue) of this solution was added to 95 mL (0.03 mmol Au) of boiling stock Au(III) solution (2.8$\times$10$^{-4}$M Au). The mixture was boiled and vigorously magnetically stirred for 2-3 minutes during which time a red-violet suspension appeared. After continuing boiling for 5 additional minutes, a light red precipitate formed on the walls of the container. The precipitate was solid gold which was not stabilized in a finely divided colloidal state by dextran.

Example 4. Preparation of Silver Hydrosol Using Aminodextran

Figure 1A:
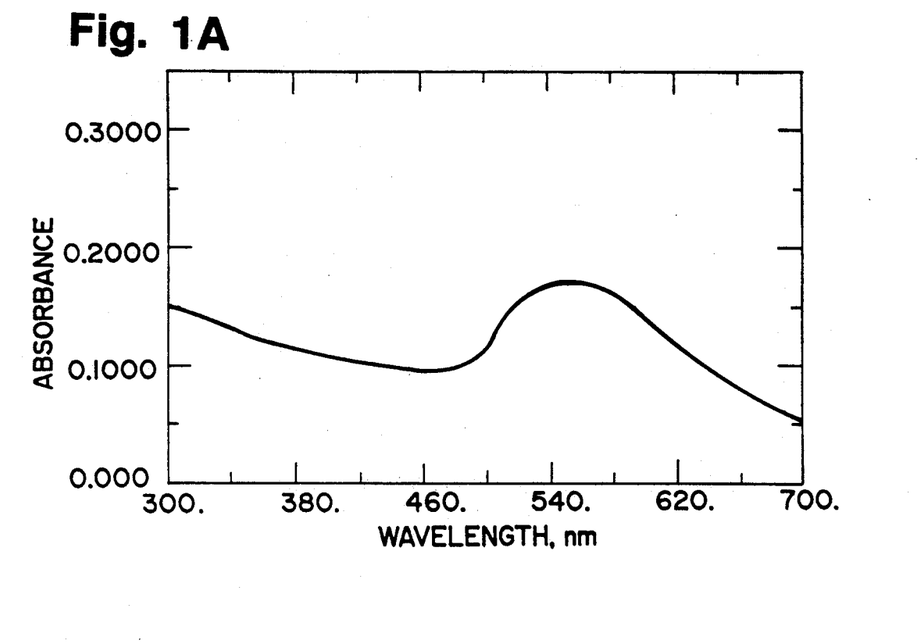
FIGS. 1A-1D illustrate an absorption extinction spectra in the visible region of gold hydrosols prepared using different aminodextran-to-Au(III) ratios according to the invention.
Figure 1B:
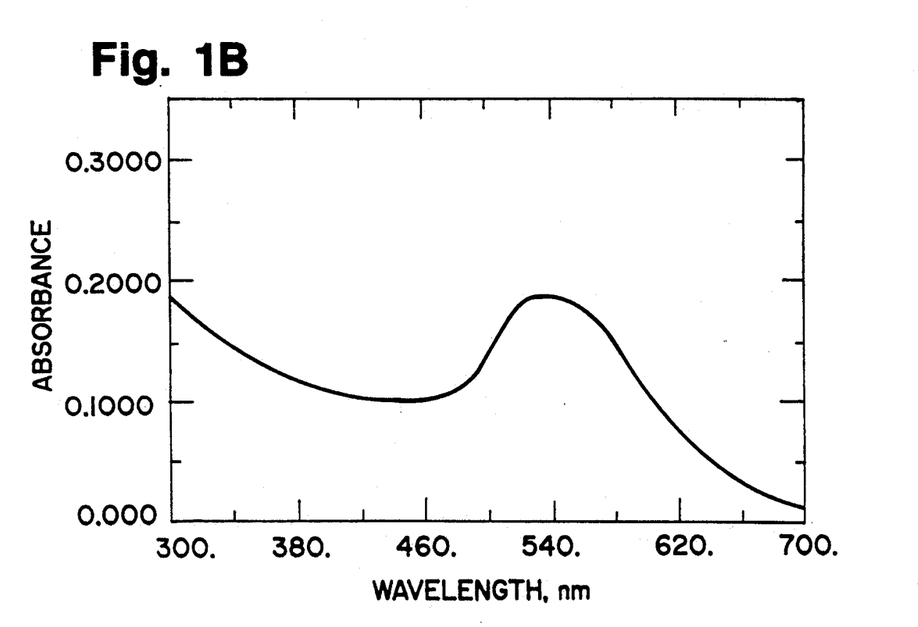
Figure 1C:
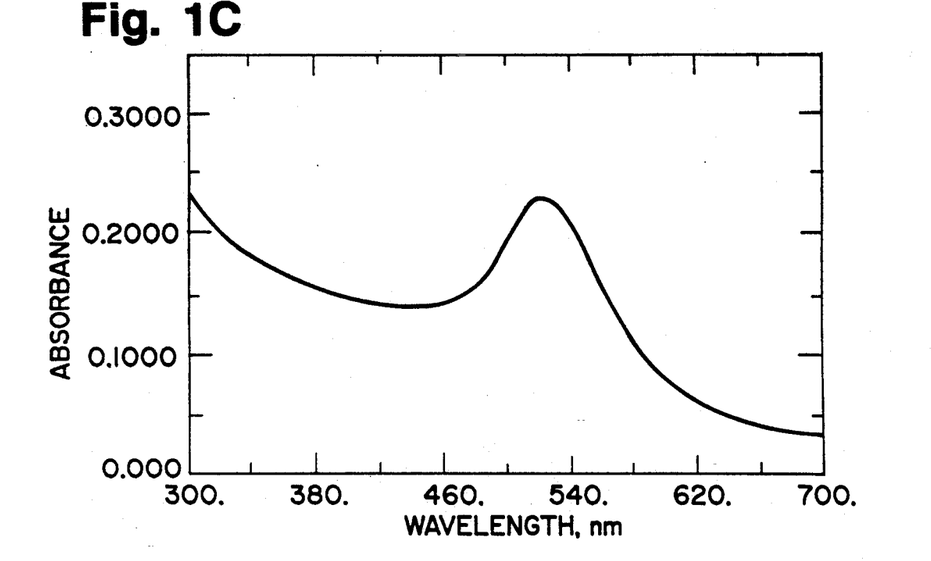
Figure 1D:
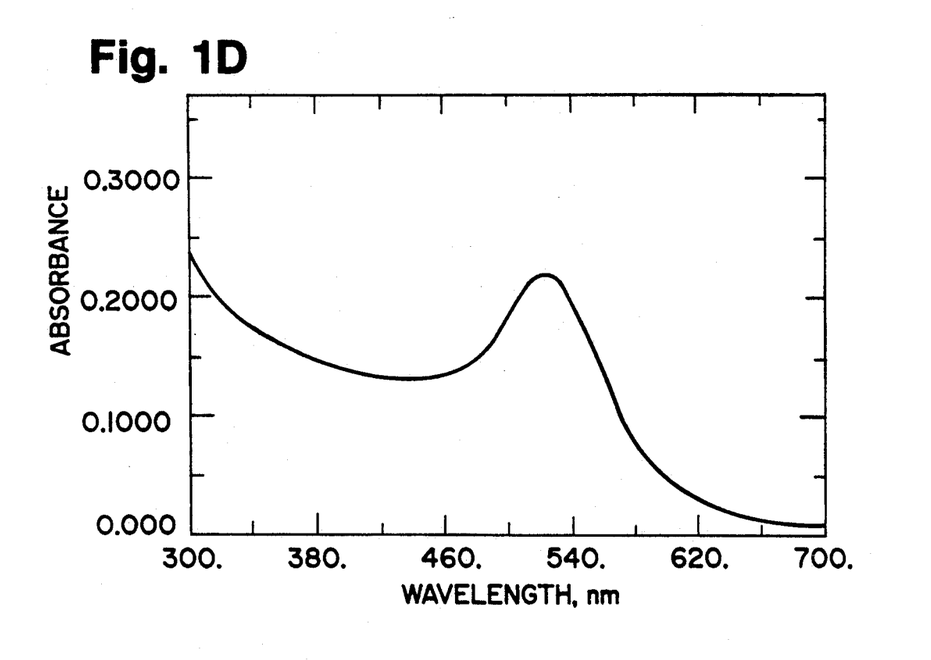
Figure 2:
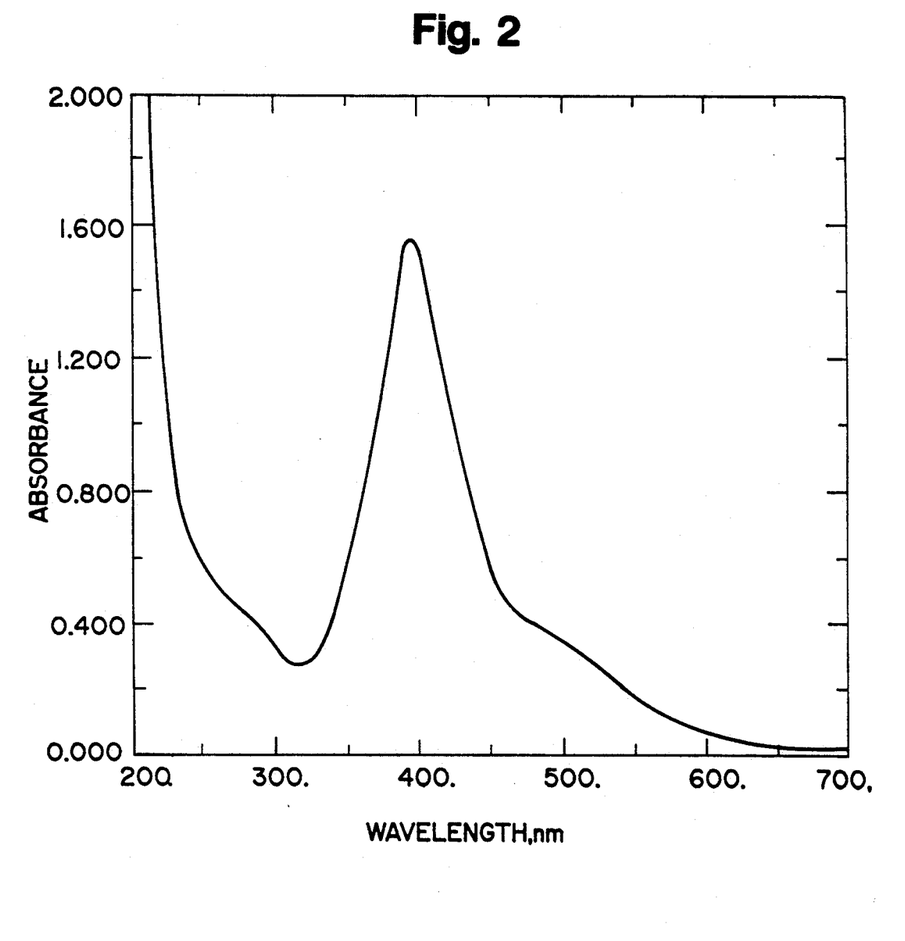
FIG. 2 illustrates an extinction spectra of a silver hydrosol prepared by mixing aqueous aminodextran T-40 and silver nitrate solutions.

135 $\mu$L of 0.589M silver nitrate (0.080 mmol Ag) solution were added to 95 mL distilled water. This solution was brought to a boil and 16.1 mL (0.6 mmol sugar residue) of aminodextran T-40 (6.2 mg/ml) were added to it. Boiling and vigorous magnetic stirring of the mixture was continued for 20 minutes, during which time the solution slowly turned yellow and then red. The suspension of silver particles was cooled to room temperature and its characteristic absorption spectrum, FIG. 2, was measured to show a peak at 395 nm and shoulder near 500 nm, and A395/A500=4.56. The same reaction, carried out in a pyrex reaction bottle at 90° C. in an oven showed no color change after. 3 hours, but did give a yellow silver sol which then turned red after about 24 hours. A parallel oven reaction between stock Au(III) solution and aminodextran at 90° C. took 3.5 hours to produce a wine red gold sol.

Figure 3A:
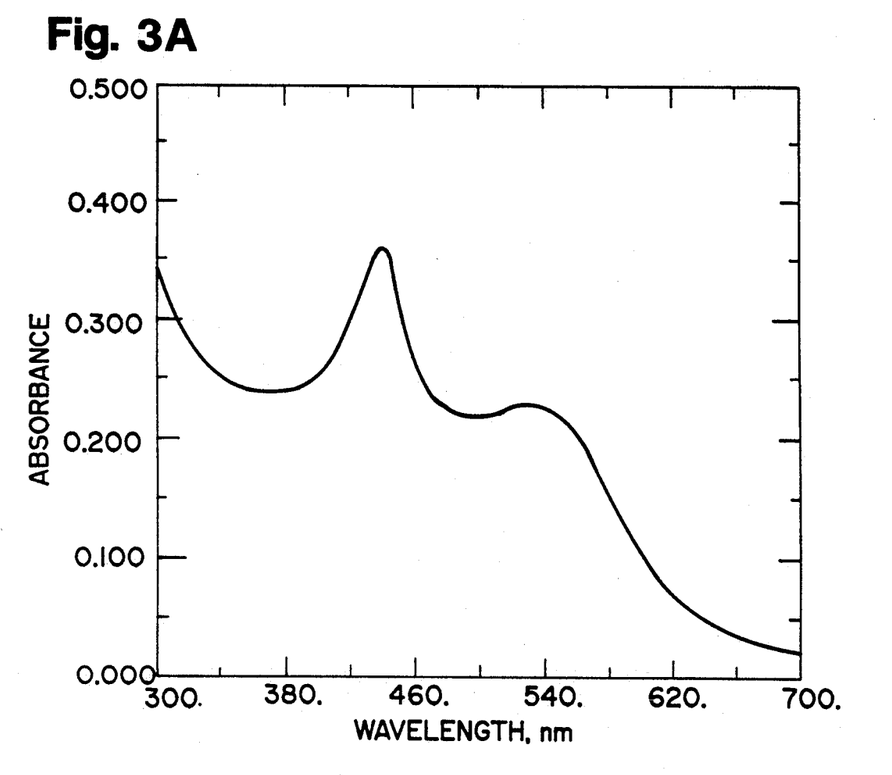
FIGS. 3A-3B illustrate an absorption spectra of FITC-dextran-Au(III) solution (FIG. 3B) and FITC-dextran-Au(III) solution mixed to near boiling temperature to produce a gold hydrosol (FIG. 3A, top spectra).
Figure 3B:
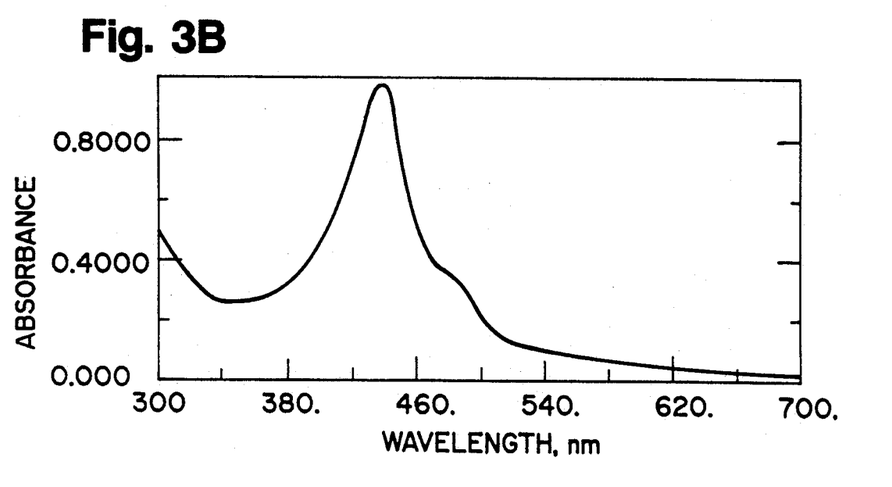

Example 5. Preparation of Gold Hydrosol Using Fluorescein Isothiocyanate (FITC)—Dextran 25 mg of FITC-dextran (Sigma; 17,000 MW; 0.01 mol FITC/mol glucose residue) was added to 5 mL of boiling stock Au(III) solution ($2.8 \times 10^{-4}$M Au). Although the solid dextran derivative dissolved in the aqueous solution no reaction was detected. After 5 minutes, an additional 10 mL of stock Au(III) solution were added to the boiling mixture and after an additional 15 minutes, the wine red color characteristic of colloidal gold was produced. Absorption spectra are displayed in FIGS. 3A and 3B. Au(III) shows an absorption peak at 420 nm and a shoulder near 480 nm, and finely divided gold particles show an additional band at 535 nm. Similar results were obtained with 25 mg FITC-dextran (2,000,000 MW; 0.004 mol FITC/mol glucose residue) in 20 ml stock Au(III) solution. The FITC-dextran gold sol was centrifuged at 20,000 rpm for 30 minutes at 15° C. in an SW60 rotor on the Beckman L8-70 ultracentrifuge, the supernatant was removed, and the mobile colloidal gold residue was redispersed in $1 \times$ phosphate buffered saline, pH 7.2. The red colloidal gold particles did not show any FITC green emission under a fluorescence microscope.

Example 6. Crosslinking of Aminodextran on Colloidal Gold 0.8 mL of 25% glutaraldehyde was added to 200 mL of approximately pH 6 colloidal gold suspension (Example 2) prepared in the presence of 0.23% w/v aminodextran. The reaction mixture was stirred for 1 hour at room temperature. Ethylenediamine (0.320 mL) was added to the reaction and the resulting mixture stirred for an additional 2 hours. In general, the diamine is selected from the group consisting of $H_2NCH_2—(CH_2)_x—CH_y(CH_3)_z—NH_2$ and $C_6H_{4+a}(NH_2)_2$, where $x=0-3$, $y=1$ or 2, and $z=1$ when $y=1$ or $Z=0$ when $y=2$; and $a=0$ or 6. Ethylenediamine is preferred. The Schiff base linkages formed by addition of the diamine were reduced by the addition of 0.303 g sodium borohydride in 2 mL of 1 mM aqueous potassium hydroxide solution and stirring the resulting reaction mixture for 30 minutes. After reduction, the mixture was exhaustively dialyzed against distilled water to a conductivity of approximately 66 μmho/cm. The dialyzed solution was then centrifuged at 25,000 rpm for about 40 minutes at 15° C. in 25 mL tubes in a Ti 50.2 rotor on a Beckman L8-70 ultracentrifuge. The mostly mobile pool of colloidal gold-aminodextran having reactive groups was easily redispersed in 100 ml of $1 \times$ phosphate buffered saline (PBS) solution. Using a 1 mm path quartz cell, an absorbance reading of 0.24–0.29 units at lambda$_{max}$=520 nm was observed. This reading indicates the presence of single particles of gold.

The mobility of T-40 derived, crosslinked aminodextran coated gold particles was measured by multi-angle Doppler electrophoretic light scattering on a Coulter DELSA 440. In aqueous solution, an average mobility of $+0.486(11) \times 10^{-4}$ cm$^2$ V$^{-1}$S$^{-1}$ was recorded over a pH range of 3.5 to 10.3. Using the Huckel equation, this data gives a zeta potential of +9 mV and establishes the coated gold particles as cationic probes. Conjugation of T11 monoclonal antibody (Coulter Immunology, Hialeah, Fla.) to the aminodextran coated particles (vide infra) did not change the cationic nature of the particles.

Example 7. Crosslinking of Aminodextran on Colloidal Gold with FITC-Dextran 0.519 mL of aminodextran, T-2M (10.3 mg/ml, 0.033 mmol glucose residue) solution were added to 10 mL of boiling stock Au(III) solution ($2.8 \times 10^{-4}$M). The mixture was boiled and vigorous magnetic stirred for 15 minutes to produce a wine-red suspension of gold particles. 26.5 mg of FITC-dextran T-2M (Sigma, 0.004 degree of substitution) dissolved in 2 mL distilled water was added to the wine-red mixture and the resulting mixture was stirred for an additional 40 minutes at room temperature. Since FITC conjugation to dextran requires primary amine groups or dextran, the Sigma material probably contains aminodextran conjugated with FITC. Consequently, crosslinking was carried out by the addition of 40 μL of 25% glutaraldehyde to the mixture and further stirring for 1 hour. To quench the crosslinking reaction, 16 μL ethylenediamine were added and the resulting mixture was stirred for 1.5 hours. Finally, 15 mg sodium borohydride in 0.1 mL of 1 mM KOH was added and mixed for 0.5 hour to stabilize the Schiff base by reduction. The borohydride reduced mixture was then centrifuged at 20,000 rpm for 30 minutes at 15° C. in an SW60 rotor, the supernatant was removed, and the mobile gold residue was redispersed in 1% BSA, 0.1% sodium azide in $1 \times$ phosphate buffered saline. These gold particles, observed under a fluorescence microscope, gave a bright green FITC emission.

Example 8. Activation of Crosslinked Aminodextran-Gold with Sulfo-SMCC

Although various sulfo-SMCC/gold ratios were tried, the best results were obtained using 2.25 μL of sulfo-SMCC (10 mg/mL in $1 \times$ PBS) per milliter of crosslinked aminodextran gold suspension. In a typical reaction, 56.25 μL of sulfo-SMCC was added to 25 mL of crosslinked aminodextran gold suspension. The mixture was mixed for 1 hour and then twice centrifuged for 30 minutes at 20,000 rpm and 15° C. The mostly mobile pool was redispersed with the aid of ultrasonic mixing, first in 25 mL and then 7.8 mL of $1 \times$ PBS. The resulting activated aminodextran gold sol was filtered through a low protein binding 0.2 μm filter prior to use.

Example 9. Activation of Antibody with 2-Iminothiolane Hydrochloride (IT)

A stock solution containing 43.77 mg/mL of T11 monoclonal antibody in $1 \times$ PBS containing 0.1% NaN$_3$ was prepared. For a reaction using 30 mg T11 antibody at a concentration of 15 mg/mL, the total reaction volume should be 2.00 mL. Using a 15:1 IT:T11 activation ratio, 2.81 μmol (0.388 mg) or 194 μL of 2 mg/mL IT in $1 \times$ PBS is required. Therefore, 1.121 mL of $1 \times$ PBS solution was added to 0.685 mL of T11 stock solution. The total volume upon mixing all the reagent solutions is 0.194 mL IT+1.121 mL PBS+0.685 mL T11=2.0 mL. The resulting solution is roller mixed for 1 hour in a reaction tube. The contents of the reaction tube were then applied to the top of a 100 mL G-50 Sephadex column, equilibrated and washed with 500 mL $1 \times$ PBS The derivatized monoclonal antibody was eluted using $1 \times$ PBS and a plurality of 5 mL fractions were collected using a UV monitor. Fractions in the middle of the band absorbing at 280 nm were pooled and the $A_{280}$ value was used to determine the T/IT product concentration. Typically, the concentration was about 2.5 mg/mL.

Example 10. Conjugation of T11/IT and Sulfo-SMCC Derivatized XL-Aminodextran Gold Particles A 2.200 mL sample of 2.854 mg/mL T11/IT in 1× PBS was added to 7.8 mL of sulfo-SMCC activated aminodextran coated gold particles prepared as described above. The T11/IT solution was added in 0.5 mL increments with sonication and rapid physical mixing between additions. The resulting suspension was then roller mixed in a 15 mL tube for approximately 2 hours. Unreacted maleimidyl groups on the sulfo-SMCC activated particles were blocked after antibody conjugation by the addition of L-cysteine. Typically, 0.120 mL of 5 mg/mL L-cysteine in 1× PBS was added to 10 mL of the conjugation mixture [(0.0120 mL L-cysteine)×(volume of conjugation mixture)] and the resulting suspension was roller mixed for about 15 minutes. The mixture was then centrifuged in a Beckman 50.2 Ti rotor for 30 minutes at 15©C and 10,000 rpm. The mostly mobile pool was resuspended in 1× PBS containing 0.1% $NaN_3$ and 1% BSA, and filtered through an 0.2 μm filter. The resulting antibody conjugated, crosslinked aminodextran coated gold particles were found suitable for use as markers in optical and electron microscopy. The high activity of T11 antibody on these gold particles was demonstrated by (1) using GAM-FITC (goat antibody against mouse immunoglobulin-FITC, Coulter Immunology) as a secondary antibody added to a mixture of T11-aminodextran-gold particles and whole blood, and observing under a fluorescence microscope that T11+ cells were completely coated with the gold label; and (2) using an inverted microscope (Zeiss) with an epi-illumination configuration to directly view the gold particles on T11+ cells as small red spots on the cell surface.

Additional successful preparations of antibody conjugated, crosslinked aminodextran coated gold particles were carried out using:

1. Aminodextran T-40 having 2× amino groups;
2. Aminodextran T-40 having 1× amino groups;
3. Aminodextran T-2M having 1× amino groups; and
4. Aminodextran T-10 having 1× amino groups.

Each of these crosslinked aminodextran coated gold particles preparations were used in three different T11 monoclonal antibody conjugation reactions. These were:

1. 1× activation with sulfo-SMCC, 0.833 mg/ml T11/IT during conjugation and no L-cysteine blocking;
2. 1× activation with sulfo-SMCC, 0.653 mg/mL T11/IT during conjugation and 0.0120× vol of 5 mg/mL L-cysteine; and
3. (1/3)× activation with sulfo-SMCC, 0.628 mg/mL T11/IT and 0.0120×vol of 5 mg/mL L-cysteine.

Example 11. Antibody-aminodextran-colloidal Metal Complexes in Cell Population Analyses Triple antibody staining of individual cells has been accomplished with colloidal gold—and two fluorochrome-conjugated antibodies (fluorescein and rhodamine or phycoerythrin plus antibody) for use in light microscopy by epi-illumination with polarized light (J. J. M. Van Dongen et al., J. Immunol. Methods, 80:1–6 (1985)) and in flow cytometry (R. Festin et al., J. Immunol. Methods, 101: 23–28 (1987)). No interference between gold (right angle light scatter) and the fluorescence labels was observed. Thus, antibody-aminodextran-colloid gold complexes can be used alone or together with fluorochrome-conjug antibodies in various cell population analyses by flow cytometry or other methods such as those described in International Patent Application WO 90/13013 by T. Russell, M. C. Hajek, C. M. Rodriquez, and W. H. Coulter. Small particles of other metals such as platinum, palladium, iridium, or rhodium, which absorb maximally in the ultraviolet region instead of visible region (gold colloid at about 520 nm; silver colloid at about 400 nm may prove to be more useful as cell labels of the antibody-aminodextran-colloidal metal type, since their absorption bands do not overlap with the emission bands of typical fluorochromes.

For analyses of T cell subsets (T4,T8) a T4 or T8 monoclonal antibody-aminodextran-gold colloid complex is first mixed with a whole blood sample ($1 \times 10^6$ total lymphocytes maximum) for 6 minutes. T4-RD1 (phycoerythrin) and T8-FITC (Coulter Immunology, Hialeah, Fla.) fluorescent markers are then added and mixed for 10 minutes. The resulting mixture is then treated by a Q-PREP (Coulter Immunology) lyse (formic acid) and quench (sodium carbonate, etc. and paraformaldehyde) of RBCs. The sample is then analyzed by flow cytometry for T4 or T8 cell populations and for T-cell specificity in the forward shifted (by colloidal metal) versus side scatter region of lymphocytes. Similar analyses have been successfully carried out with T4- and T8- polystyrene bead (ca. 2 μm diameter) conjugates for analyses of T4 and T8 cell populations among lymphocytes in whole blood. It is important that bead or metal particle-antibody conjugates be first mixed with whole blood before adding fluorescent markers to avoid saturation of antigenic sites on T-cells by the smaller and more mobile molecular dye-antibody conjugates.

Shifts in the forward versus side scatter diagrams for metal colloid-labelled lymphocytes will differ in degree and direction depending on the size, shape and refractive index of metal particles. Therefore, it is conceivable that two or more colloidal particles using different colloidal metals can be conjugated with different monoclonal antibodies and used to analyze cell subset populations in non-overlapping regions of the scatter plot by flow cytometry with multiple fluorescent markers. This would be useful to investigate diversity among antigenic sites expressed in is small population of cells, such as, about $10^6$ cells.

I claim:

1. A method for preparing colloidal metal(O) particles from a solution of a metal salt and coating said particles with a polymeric organic compound which also is used as a reductant for said metal salt, said method comprising:
   (a) heating a solution containing an amine derivatized, oxidizable sugar containing polysaccharide and a metal salt capable of being reduced by said oxidizable sugar containing polysaccharide for a time and at a temperature sufficient to reduce said metal salt to colloidal metal particles and simultaneously coating said particles with said polysaccharide; and
   (b) stabilizing the amine derivatized polysaccharide coating on said particles by means of a bifunctional crosslinking agent, a diamine and a reducing agent.

2. The method of claim 1 wherein said amine derivatized polysaccharide is an aminodextran.

3. The method of claim 1 wherein said metal salt has a reduction potential of +0.7 volts or higher.

4. The method of claim 3 wherein said metal salt is selected from the group consisting of gold, silver, platinum, palladium, rhodium and iridium salts capable of being reduced by said polysaccharide.

5. The method of claim 4 wherein said metal salt is a gold or silver salt.

6. A method of preparing colloidal metal(O) particles coated with an amine derivatized, oxidizable sugar containing polysaccharide, said method comprising:
   (a) heating an aqueous solution of a sugar reducible metal salt and adding to said solution an aqueous solution of an amine derivatized polysaccharide having at least one reducing sugar component;
   (b) heating and mixing the solution resulting from step (a) for about 10–30 minutes at a temperature in the range of about 90°–100° C. to reduce said metal salt by said polysaccharide to colloidal metal(O) particles suspended in said polysaccharide solution and coated with said polysaccharide;
   (c) cooling the solution resulting from step (b) to room temperature and adding to the cooled solution an aqueous first bifunctional reagent capable of reacting with amine groups on said amine derivatized polysaccharide;
   (d) adding an organic diamine to the product of step (c);
   (e) reducing the reducible groups formed in step (d);
   (f) dialyzing the solution of step (e) against water; and
   (g) centrifuging the product of step (f) to obtain amine derivatized polysaccharide coated particles capable of being dispersed as colloids.

7. The method of claim 6 wherein said derivatized polysaccharide is an aminodextran.

8. The method of claim 6 wherein said metal salt has a reduction potential of +0.7 volts or higher.

9. The method of claim 8 wherein said metal salt is selected from the group consisting of gold, silver, platinum, palladium, rhodium and iridium salts capable of being reduced by said polysaccharide.

10. The method of claim 9 wherein said metal salt is selected from the group consisting a gold or silver salt.

11. The method of claim 6 wherein said first bifunctional reagent is glutaraldehyde.

12. The method of claim 6 wherein said diamine is selected from the group consisting of $H_2NCH_2-(CH_2)_x-CH_y(CH_3)_z-NH_2$ and $C_6H_{4+a}(NH_2)_2$, where $x=0-3$, $y=1$ or $2$, and $Z=1$ when $y=1$ or $Z=0$ when $y=2$; and $a=0$ or $6$.

13. A method of preparing colloidal metal(O) particles coated with an amine derivatized, oxidizable sugar containing polysaccharide and having a protein bound thereto, said method comprising:
   (a) preparing coated colloidal metal particles according to claim 1; and
   (b) reacting the particles of step (a) with a protein capable of forming a covalent bond with the amine groups present on said particles.

14. The method of to claim 13 wherein said protein is a monoclonal antibody.

15. The method according to claim 13 wherein said colloidal metal particles are selected from the group consisting of colloidal gold, silver, platinum, palladium, rhodium and iridium colloidal particles.

16. The method of claim 15 wherein said colloidal particles are colloidal gold or silver particles.

17. A method of preparing colloidal metal(O) particles coated with an amine-derivatized reducible sugar containing polysaccharide and having a protein bound thereto, said method comprising:
   (a) preparing colloidal metal particles according to claim 1;
   (b) converting the amine groups present on said particles to a group selected from the group consisting of sulhydryl and maleimidyl groups; and
   (c) reacting the product of step (b) with:
      (1) a protein having a functional group reactive with said sulfhydryl and maleimidyl groups or
      (2) a derivatized protein having at least one functional group selected from the group consisting of sulfhydryl and maleimidyl groups, such that when said particles contain sulfhydryl groups said proteins contains maleimidyl groups and when said particles contain maleimidyl groups said protein contains sulfhydryl groups.

18. The method of claim 17 wherein said protein is selected from the group consisting of a monoclonal and a polyclonal antibody either with or with a detectable label selected from the group consisting of an enzyme, a dye, an electron dense element and a substance containing a radioactive element.

19. The method of claim 17 wherein said colloidal metal particles are selected from the group consisting of colloidal gold, silver, platinum, palladium, rhodium and iridium colloidal particles.

20. The method of claim 19 wherein said colloidal particles are gold or silver colloidal particles.

21. Colloidal metal(O) particles having a polymeric organic coating thereon of a substance used to form said metal(O) particles by reduction of a metal salt with said substance, said coating comprising a stabilized amine derivatized polysaccharide and said coating being stabilized by means of a bifunctional crosslinking agent, a diamine and a reducing agent.

22. The particles of claim 21 wherein said amine derivatized polysaccharide is an aminodextran.

23. The particles of claim 21 wherein said bifunctional crosslinking agent is glutaraldehyde.

24. The particles of claim 21 wherein said diamine is selected from the group consisting of $H_2NCH_2-(CH_2)_x-CH_y(CH_3)_z-NH_2$ and $C_6H_{4+a}(NH_2)_2$, where $x=0-3$, $y=1$ or $2$, and $Z=1$ when $y=1$ or $Z=0$ when $y=2$; and $a=0$ or $6$.

25. The particles of claim 21 wherein said metal(O) is selected from the group consisting of gold, silver, platinum, palladium, rhodium and iridium.

26. The particle of claim 25 wherein said metal(O) is silver or gold.

27. Coated colloidal metal particles having a protein bound thereto, said particles comprising colloidal metal(O) particles coated with a stabilized amine derivatized polysaccharide and a protein bound to said coating, said coating being stabilized by means of a bifunctional crosslinking agent, a diamine and a reducing agent, and said metal(O) particles being formed by reduction of a metal salt with said amine derivatized polysaccharide.

28. The particles of claim 27 wherein said amine derivatized polysaccharide is an aminodextran.

29. The particles of claim 27 wherein said bifunctional crosslinking reagent is glutaraldehyde.

30. The particles of claim 27 wherein said metal(O) is selected from the group consisting of gold, silver, platinum, palladium, rhodium and iridium.

31. The particles of claim 30 wherein said metal(O) is gold or silver.

32. The particle of claim 27 wherein said diamine is selected from the group consisting of $H_2NCH_2-(CH_2)_x-CH_y(CH_3)_z-NH_2$ and $C_6H_{4+a}(NH_2)_2$, where x=0-3, y=1 or 2, and Z=1 when y=1 or Z=0 when y=2; and a=0 or 6.

33. The particles according to claim 27 wherein said protein is selected from the group consisting of polyclonal antibodies, monoclonal antibodies, enzymes and lectins.

34. The particles according to claim 27 wherein said protein is a monoclonal or polyclonal antibody.

35. The particles according to claim 27 wherein said protein has a detectible enzyme or a substance containing a radioactive element or a dye attached thereto.

36. The particles according to claim 27 wherein said stabilized amine derivatized polysaccharide coated particles coated are reacted with selected reagents to produce particles having either reactive maleimidyl or sulfhydryl groups attached to said polysaccharide coating and said protein is covalently bound to the sulfhydryl or maleimidyl group on said coated particles.

37. Particles according to claim 36 wherein said protein is derivatized to contain either reactive sulfhydryl or maleimidyl groups prior to binding said protein to said maleimidyl or sulfhydryl containing polysaccharide coated particles, provided that when said particles contain sulfhydryl groups said protein contains maleimidyl groups and when said particles contain maleimidyl groups said protein contains sulfhydryl groups.

* * * * *

UNITED STATES PATENT AND TRADEMARK OFFICE
CERTIFICATE OF CORRECTION

PATENT NO. : 5,248,772

DATED : September 28, 1993

INVENTOR(S) : Olavi Siiman and Alexander Burshteyn

It is certified that error appears in the above-indentified patent and that said Letters Patent is hereby corrected as shown below:

Column 1, line 36, change "force" to --forces--;

Column 4, lines 17-18, change ")e-thyl]sulfone" to
--)-ethyl]sulfone--;

Column 6, line 14, after "($H_3IO_6/IO_3-$)" delete --,--;

Column 9, line 30, change "$C_{46}H_{79}NO_{37} \cdot 3H_2O$" to
--$C_{46}H_{79}NO_{37} \cdot 3H_2O$--;

line 30, change "42 76" to --42.76--;

line 37, change "$C_{46}H_{79}NO_{37} \cdot 3H_2O$" to
--$C_{46}H_{79}NO_{37} \cdot 3H_2O$--;

line 44, change "$C_{49}H_{84}NO_{40} \cdot 3H_2O$" to
--$C_{49}H_{84}NO_{40} \cdot 3H_2O$--;

Column 10, line 10, change "   >" to --  - --> --;

line 68, change "after.3" to --after 3--;

Column 11, line 65, change "$V^-s^{-1}$" to --$V^{-1}s^{-1}$--;

Column 13, line 23, change "15©C" to --15°C--;

UNITED STATES PATENT AND TRADEMARK OFFICE
CERTIFICATE OF CORRECTION

PATENT NO. : 5,248,772

DATED : September 28, 1993

INVENTOR(S) : Olavi Siiman and Alexander Burshteyn

It is certified that error appears in the above-indentified patent and that said Letters Patent is hereby corrected as shown below:

Column 16, line 24, change "with or with" to --with or without--;

Column 16, line 68, change "reagent" to --agent--.

Signed and Sealed this

Twelfth Day of April, 1994

Attest:

BRUCE LEHMAN

*Attesting Officer*    *Commissioner of Patents and Trademarks*